(12) United States Patent
Fan et al.

(10) Patent No.: US 11,564,945 B2
(45) Date of Patent: Jan. 31, 2023

(54) CHIMERIC ANTIGEN RECEPTOR AND USE THEREOF

(71) Applicant: Nanjing Legend Biotech Co., Ltd., Jiangsu (CN)

(72) Inventors: Xiaohu Fan, Edmonton (CA); Qiuchuan Zhuang, Jiangsu (CN); Pingyan Wang, Anhui (CN); Lei Yang, Anhui (CN); Xiujun Zheng, Jiangsu (CN); Jiaying Hao, Jiangsu (CN); Shaobo Liu, Jiangsu (CN)

(73) Assignee: Nanjing Legend Biotech Co., Ltd., Jiangsu (CN)

( * ) Notice: Subject to any disclaimer, the term of this patent is extended or adjusted under 35 U.S.C. 154(b) by 761 days.

(21) Appl. No.: 16/474,735

(22) PCT Filed: Dec. 29, 2017

(86) PCT No.: PCT/CN2017/119711
§ 371 (c)(1),
(2) Date: Jun. 28, 2019

(87) PCT Pub. No.: WO2018/121712
PCT Pub. Date: Jul. 5, 2018

(65) Prior Publication Data
US 2019/0321404 A1 Oct. 24, 2019

(30) Foreign Application Priority Data
Dec. 30, 2016 (CN) .......................... 201611263835.1

(51) Int. Cl.
| | | |
|---|---|---|
| *A61K 35/17* | (2015.01) | |
| *C07K 14/725* | (2006.01) | |
| *C07K 16/30* | (2006.01) | |
| *C07K 16/32* | (2006.01) | |
| *C12N 5/0735* | (2010.01) | |
| *C12N 5/0775* | (2010.01) | |
| *C12N 15/62* | (2006.01) | |
| *A61K 45/06* | (2006.01) | |

(52) U.S. Cl.
CPC .......... *A61K 35/17* (2013.01); *C07K 14/7051* (2013.01); *C07K 16/30* (2013.01); *C07K 16/32* (2013.01); *C12N 5/0606* (2013.01); *C12N 5/0663* (2013.01); *C12N 15/62* (2013.01); *A61K 45/06* (2013.01)

(58) Field of Classification Search
CPC ...................................................... A61K 35/17
See application file for complete search history.

(56) References Cited

U.S. PATENT DOCUMENTS

| | | | | |
|---|---|---|---|---|
| 2013/0316366 | A1* | 11/2013 | Yu .......................... | C12N 15/86 |
| | | | | 435/320.1 |
| 2017/0275366 | A1* | 9/2017 | Schiffer-Mannioui ...................... | |
| | | | | A61P 35/00 |

FOREIGN PATENT DOCUMENTS

| | | | | | |
|---|---|---|---|---|---|
| CN | 102120772 | * | 5/2013 | ............. | C07K 19/00 |
| CN | 105418765 | A | 3/2016 | | |
| WO | WO2012/079000 | * | 6/2012 | ............. | C07H 21/04 |
| WO | WO2013/033626 | * | 7/2013 | ............. | C12N 15/62 |
| WO | 2016012623 | A1 | 1/2016 | | |
| WO | WO2016/014789 | * | 1/2016 | ............. | A61K 48/00 |
| WO | 2016016344 | A1 | 2/2016 | | |
| WO | 2016034666 | A1 | 3/2016 | | |

OTHER PUBLICATIONS

Chekmasova et al. (Blood (2015) 126 (23) : 3094, http://doi.org/10.1182/blood.V126.23.3094.3094). (Year: 2015).*

* cited by examiner

*Primary Examiner* — Scott Long
(74) *Attorney, Agent, or Firm* — Ice Miller LLP

(57) ABSTRACT

Disclosed herein is a novel chimeric antigen receptor and use thereof. The novel chimeric antigen receptor consists of a signal peptide, an antigen binding domain, a transmembrane region, and an intracellular signal domain, and comprises a 4-1BB signal peptide and/or a 4-1BB molecular transmembrane region. Nucleic acid sequences of various chimeric antigen receptors are separated and purified and provided is a chimeric antigen receptor and a CAR-T cell which are specific for a CD19 malignant tumor antigen. In the malignant tumor killing test of hematological cell lines, the ability of immune cells to target and recognize tumor cells is significantly enhanced, and the killing activity against tumor cells is also enhanced.

22 Claims, 5 Drawing Sheets

Specification includes a Sequence Listing.

SEQUENCE LISTING

```
<160> NUMBER OF SEQ ID NOS: 24

<210> SEQ ID NO 1
<211> LENGTH: 27
<212> TYPE: PRT
<213> ORGANISM: Artificial Sequence
<220> FEATURE:
<223> OTHER INFORMATION: 4-1BB transmembrane region

<400> SEQUENCE: 1

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 2
<211> LENGTH: 23
<212> TYPE: PRT
<213> ORGANISM: artificial sequence
<220> FEATURE:
<223> OTHER INFORMATION: 4-1BB signal peptide

<400> SEQUENCE: 2

Met Gly Asn Ser Cys Tyr Asn Ile Val Ala Thr Leu Leu Leu Val Leu
1               5                   10                  15

Asn Phe Glu Arg Thr Arg Ser
            20

<210> SEQ ID NO 3
<211> LENGTH: 21
<212> TYPE: PRT
<213> ORGANISM: artificial sequence
<220> FEATURE:
<223> OTHER INFORMATION: CD8a signal peptide

<400> SEQUENCE: 3

Met Ala Leu Pro Val Thr Ala Leu Leu Leu Pro Leu Ala Leu Leu Leu
1               5                   10                  15

His Ala Ala Arg Pro
            20

<210> SEQ ID NO 4
<211> LENGTH: 48
<212> TYPE: PRT
<213> ORGANISM: artificial sequence
<220> FEATURE:
<223> OTHER INFORMATION: CD8a hinge region

<400> SEQUENCE: 4
```

-continued

```
Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
                20                  25                  30

Ala Ala Gly Gly Ala Val His Thr Arg Gly Leu Asp Phe Ala Cys Asp
            35                  40                  45
```

<210> SEQ ID NO 5
<211> LENGTH: 21
<212> TYPE: PRT
<213> ORGANISM: artificial sequence
<220> FEATURE:
<223> OTHER INFORMATION: CD8a transmembrane region

<400> SEQUENCE: 5

```
Ile Tyr Ile Trp Ala Pro Leu Ala Gly Thr Cys Gly Val Leu Leu Leu
1               5                   10                  15

Ser Leu Val Ile Thr
                20
```

<210> SEQ ID NO 6
<211> LENGTH: 42
<212> TYPE: PRT
<213> ORGANISM: artificial sequence
<220> FEATURE:
<223> OTHER INFORMATION: 4-1BB intracellular co-stimulatory signal
      domain

<400> SEQUENCE: 6

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40
```

<210> SEQ ID NO 7
<211> LENGTH: 41
<212> TYPE: PRT
<213> ORGANISM: artificial sequence
<220> FEATURE:
<223> OTHER INFORMATION: CD28 intracellular co-stimulatory signal domain

<400> SEQUENCE: 7

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40
```

<210> SEQ ID NO 8
<211> LENGTH: 113
<212> TYPE: PRT
<213> ORGANISM: artificial sequence
<220> FEATURE:
<223> OTHER INFORMATION: CD3z intracellular signalling domain

<400> SEQUENCE: 8

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30
```

```
Asp Val Leu Asp Lys Arg Arg Gly Arg Asp Pro Glu Met Gly Gly Lys
                35                  40                  45

Pro Gln Arg Arg Lys Asn Pro Gln Glu Gly Leu Tyr Asn Glu Leu Gln
 50                  55                  60

Lys Asp Lys Met Ala Glu Ala Tyr Ser Glu Ile Gly Met Lys Gly Glu
 65                  70                  75                  80

Arg Arg Arg Gly Lys Gly His Asp Gly Leu Tyr Gln Gly Leu Ser Thr
                 85                  90                  95

Ala Thr Lys Asp Thr Tyr Asp Ala Leu His Met Gln Ala Leu Pro Pro
                100                 105                 110

Arg
```

<210> SEQ ID NO 9
<211> LENGTH: 259
<212> TYPE: PRT
<213> ORGANISM: artificial sequence
<220> FEATURE:
<223> OTHER INFORMATION: CD19 antigen binding domain

<400> SEQUENCE: 9

```
Glu Val Lys Leu Gln Glu Ser Gly Pro Gly Leu Val Ala Pro Ser Gln
 1               5                  10                  15

Ser Leu Ser Val Thr Cys Thr Val Ser Gly Val Ser Leu Pro Asp Tyr
                20                  25                  30

Gly Val Ser Trp Ile Arg Gln Pro Pro Arg Lys Gly Leu Glu Trp Leu
                35                  40                  45

Gly Val Ile Trp Gly Ser Glu Thr Thr Tyr Tyr Asn Ser Ala Leu Lys
 50                  55                  60

Ser Arg Leu Thr Ile Ile Lys Asp Asn Ser Lys Ser Gln Val Phe Leu
 65                  70                  75                  80

Lys Met Asn Ser Leu Gln Thr Asp Asp Thr Ala Ile Tyr Tyr Cys Ala
                 85                  90                  95

Lys His Tyr Tyr Tyr Gly Gly Ser Tyr Ala Met Asp Tyr Trp Gly Gln
                100                 105                 110

Gly Thr Ser Val Thr Val Ser Ser Gly Gly Gly Ser Gly Gly Gly Ser
                115                 120                 125

Gly Gly Gly Ser Gly Gly Ser Asp Ile Gln Met Thr Gln Thr Thr
130                 135                 140

Ser Ser Leu Ser Ala Ser Leu Gly Asp Arg Val Thr Ile Ser Cys Arg
145                 150                 155                 160

Ala Ser Gln Asp Ile Ser Lys Tyr Leu Asn Trp Tyr Gln Gln Lys Pro
                165                 170                 175

Asp Gly Thr Val Lys Leu Leu Ile Tyr His Thr Ser Arg Leu His Ser
                180                 185                 190

Gly Val Pro Ser Arg Phe Ser Gly Ser Gly Ser Gly Thr Asp Tyr Ser
                195                 200                 205

Leu Thr Ile Ser Asn Leu Glu Gln Glu Asp Ile Ala Thr Tyr Phe Cys
                210                 215                 220

Gln Gln Gly Asn Thr Leu Pro Tyr Thr Phe Gly Gly Gly Thr Lys Leu
225                 230                 235                 240

Glu Ile Thr Arg Ala Asp Ala Ala Pro Thr Val Ser Ile Phe Pro Pro
                245                 250                 255

Ser Ser Asn
```

-continued

<210> SEQ ID NO 10
<211> LENGTH: 463
<212> TYPE: PRT
<213> ORGANISM: artificial sequence
<220> FEATURE:
<223> OTHER INFORMATION: 4-1BB signal peptide-VH-(G3S)4-VL-4-1BB
      TM-4-1BB cyto-CD3z

<400> SEQUENCE: 10

Met Gly Asn Ser Cys Tyr Asn Ile Val Ala Thr Leu Leu Val Leu
1               5                   10                  15

Asn Phe Glu Arg Thr Arg Ser Glu Val Lys Leu Gln Glu Ser Gly Pro
            20                  25                  30

Gly Leu Val Ala Pro Ser Gln Ser Leu Ser Val Thr Cys Thr Val Ser
            35                  40                  45

Gly Val Ser Leu Pro Asp Tyr Gly Val Ser Trp Ile Arg Gln Pro Pro
        50                  55                  60

Arg Lys Gly Leu Glu Trp Leu Gly Val Ile Trp Gly Ser Glu Thr Thr
65              70                  75                  80

Tyr Tyr Asn Ser Ala Leu Lys Ser Arg Leu Thr Ile Ile Lys Asp Asn
                85                  90                  95

Ser Lys Ser Gln Val Phe Leu Lys Met Asn Ser Leu Gln Thr Asp Asp
            100                 105                 110

Thr Ala Ile Tyr Tyr Cys Ala Lys His Tyr Tyr Gly Gly Ser Tyr
            115                 120                 125

Ala Met Asp Tyr Trp Gly Gln Gly Thr Ser Val Thr Val Ser Ser Gly
        130                 135                 140

Gly Gly Ser Gly Gly Gly Ser Gly Gly Gly Ser Gly Gly Gly Ser Asp
145                 150                 155                 160

Ile Gln Met Thr Gln Thr Thr Ser Ser Leu Ser Ala Ser Leu Gly Asp
                165                 170                 175

Arg Val Thr Ile Ser Cys Arg Ala Ser Gln Asp Ile Ser Lys Tyr Leu
            180                 185                 190

Asn Trp Tyr Gln Gln Lys Pro Asp Gly Thr Val Lys Leu Leu Ile Tyr
        195                 200                 205

His Thr Ser Arg Leu His Ser Gly Val Pro Ser Arg Phe Ser Gly Ser
        210                 215                 220

Gly Ser Gly Thr Asp Tyr Ser Leu Thr Ile Ser Asn Leu Glu Gln Glu
225                 230                 235                 240

Asp Ile Ala Thr Tyr Phe Cys Gln Gln Gly Asn Thr Leu Pro Tyr Thr
                245                 250                 255

Phe Gly Gly Gly Thr Lys Leu Glu Ile Thr Arg Ala Asp Ala Ala Pro
            260                 265                 270

Thr Val Ser Ile Phe Pro Pro Ser Ser Asn Ile Ile Ser Phe Phe Leu
        275                 280                 285

Ala Leu Thr Ser Thr Ala Leu Leu Phe Leu Leu Phe Phe Leu Thr Leu
        290                 295                 300

Arg Phe Ser Val Val Lys Arg Gly Arg Lys Lys Leu Leu Tyr Ile Phe
305                 310                 315                 320

Lys Gln Pro Phe Met Arg Pro Val Gln Thr Thr Gln Glu Glu Asp Gly
                325                 330                 335

Cys Ser Cys Arg Phe Pro Glu Glu Glu Glu Gly Gly Cys Glu Leu Arg
            340                 345                 350

Val Lys Phe Ser Arg Ser Ala Asp Ala Pro Ala Tyr Gln Gln Gly Gln
        355                 360                 365

-continued

Asn Gln Leu Tyr Asn Glu Leu Asn Leu Gly Arg Arg Glu Glu Tyr Asp
    370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
                435                 440                 445

Lys Asp Thr Tyr Asp Ala Leu His Met Gln Ala Leu Pro Pro Arg
450                 455                 460

<210> SEQ ID NO 11
<211> LENGTH: 503
<212> TYPE: PRT
<213> ORGANISM: artificial sequence
<220> FEATURE:
<223> OTHER INFORMATION: CD8a signal peptide-VH-(G3S)4-VL-CD8a hinge
      TM-4-1BB cyto-CD3z

<400> SEQUENCE: 11

Met Ala Leu Pro Val Thr Ala Leu Leu Leu Pro Leu Ala Leu Leu Leu
1               5                   10                  15

His Ala Ala Arg Pro Glu Val Lys Leu Gln Glu Ser Gly Pro Gly Leu
            20                  25                  30

Val Ala Pro Ser Gln Ser Leu Ser Val Thr Cys Thr Val Ser Gly Val
        35                  40                  45

Ser Leu Pro Asp Tyr Gly Val Ser Trp Ile Arg Gln Pro Pro Arg Lys
    50                  55                  60

Gly Leu Glu Trp Leu Gly Val Ile Trp Gly Ser Glu Thr Thr Tyr Tyr
65                  70                  75                  80

Asn Ser Ala Leu Lys Ser Arg Leu Thr Ile Ile Lys Asp Asn Ser Lys
                85                  90                  95

Ser Gln Val Phe Leu Lys Met Asn Ser Leu Gln Thr Asp Asp Thr Ala
            100                 105                 110

Ile Tyr Tyr Cys Ala Lys His Tyr Tyr Tyr Gly Gly Ser Tyr Ala Met
        115                 120                 125

Asp Tyr Trp Gly Gln Gly Thr Ser Val Thr Val Ser Ser Gly Gly Gly
    130                 135                 140

Ser Gly Gly Gly Ser Gly Gly Gly Ser Gly Gly Gly Ser Asp Ile Gln
145                 150                 155                 160

Met Thr Gln Thr Thr Ser Ser Leu Ser Ala Ser Leu Gly Asp Arg Val
                165                 170                 175

Thr Ile Ser Cys Arg Ala Ser Gln Asp Ile Ser Lys Tyr Leu Asn Trp
            180                 185                 190

Tyr Gln Gln Lys Pro Asp Gly Thr Val Lys Leu Leu Ile Tyr His Thr
        195                 200                 205

Ser Arg Leu His Ser Gly Val Pro Ser Arg Phe Ser Gly Ser Gly Ser
    210                 215                 220

Gly Thr Asp Tyr Ser Leu Thr Ile Ser Asn Leu Glu Gln Glu Asp Ile
225                 230                 235                 240

Ala Thr Tyr Phe Cys Gln Gln Gly Asn Thr Leu Pro Tyr Thr Phe Gly
                245                 250                 255

Gly Gly Thr Lys Leu Glu Ile Thr Arg Ala Asp Ala Ala Pro Thr Val
            260                 265                 270

```
Ser Ile Phe Pro Pro Ser Ser Asn Ala Lys Pro Thr Thr Thr Pro Ala
            275                 280                 285

Pro Arg Pro Pro Thr Pro Ala Pro Thr Ile Ala Ser Gln Pro Leu Ser
        290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Lys Arg Gly
            340                 345                 350

Arg Lys Lys Leu Leu Tyr Ile Phe Lys Gln Pro Phe Met Arg Pro Val
        355                 360                 365

Gln Thr Thr Gln Glu Glu Asp Gly Cys Ser Cys Arg Phe Pro Glu Glu
370                 375                 380

Glu Glu Gly Gly Cys Glu Leu Arg Val Lys Phe Ser Arg Ser Ala Asp
385                 390                 395                 400

Ala Pro Ala Tyr Gln Gln Gly Gln Asn Gln Leu Tyr Asn Glu Leu Asn
                405                 410                 415

Leu Gly Arg Arg Glu Glu Tyr Asp Val Leu Asp Lys Arg Arg Gly Arg
            420                 425                 430

Asp Pro Glu Met Gly Gly Lys Pro Arg Arg Lys Asn Pro Gln Glu Gly
        435                 440                 445

Leu Tyr Asn Glu Leu Gln Lys Asp Lys Met Ala Glu Ala Tyr Ser Glu
450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
                485                 490                 495

Met Gln Ala Leu Pro Pro Arg
            500

<210> SEQ ID NO 12
<211> LENGTH: 463
<212> TYPE: PRT
<213> ORGANISM: artificial sequence
<220> FEATURE:
<223> OTHER INFORMATION: CD8a signal peptide-VH-(G3S)4-VL-4-1BB TM-4-1BB
      cyto-CD3z

<400> SEQUENCE: 12

Met Ala Leu Pro Val Thr Ala Leu Leu Leu Pro Leu Ala Leu Leu Leu
1               5                   10                  15

His Ala Ala Arg Pro Glu Val Lys Leu Gln Glu Ser Gly Pro Gly Leu
            20                  25                  30

Val Ala Pro Ser Gln Ser Leu Ser Val Thr Cys Thr Val Ser Gly Val
        35                  40                  45

Ser Leu Pro Asp Tyr Gly Val Ser Trp Ile Arg Gln Pro Pro Arg Lys
    50                  55                  60

Gly Leu Glu Trp Leu Gly Val Ile Trp Gly Ser Glu Thr Thr Tyr Tyr
65                  70                  75                  80

Asn Ser Ala Leu Lys Ser Arg Leu Thr Ile Ile Lys Asp Asn Ser Lys
                85                  90                  95

Ser Gln Val Phe Leu Lys Met Asn Ser Leu Gln Thr Asp Asp Thr Ala
            100                 105                 110

Ile Tyr Tyr Cys Ala Lys His Tyr Tyr Tyr Gly Gly Ser Tyr Ala Met
```

```
            115                 120                 125
Asp Tyr Trp Gly Gln Gly Thr Ser Val Thr Val Ser Ser Gly Gly
130                 135                 140

Ser Gly Gly Gly Ser Gly Gly Ser Gly Gly Ser Asp Ile Gln
145                 150                 155                 160

Met Thr Gln Thr Thr Ser Ser Leu Ser Ala Ser Leu Gly Asp Arg Val
                165                 170                 175

Thr Ile Ser Cys Arg Ala Ser Gln Asp Ile Ser Lys Tyr Leu Asn Trp
            180                 185                 190

Tyr Gln Gln Lys Pro Asp Gly Thr Val Lys Leu Leu Ile Tyr His Thr
                195                 200                 205

Ser Arg Leu His Ser Gly Val Pro Ser Arg Phe Ser Gly Ser Gly Ser
210                 215                 220

Gly Thr Asp Tyr Ser Leu Thr Ile Ser Asn Leu Glu Gln Glu Asp Ile
225                 230                 235                 240

Ala Thr Tyr Phe Cys Gln Gln Gly Asn Thr Leu Pro Tyr Thr Phe Gly
                245                 250                 255

Gly Gly Thr Lys Leu Glu Ile Thr Arg Ala Asp Ala Ala Pro Thr Val
            260                 265                 270

Ser Ile Phe Pro Pro Ser Ser Asn Thr Ser Ile Ile Ser Phe Leu
            275                 280                 285

Ala Leu Thr Ser Thr Ala Leu Leu Phe Leu Leu Phe Phe Leu Thr Leu
            290                 295                 300

Arg Phe Ser Val Val Lys Arg Gly Arg Lys Lys Leu Leu Tyr Ile Phe
305                 310                 315                 320

Lys Gln Pro Phe Met Arg Pro Val Gln Thr Thr Gln Glu Glu Asp Gly
                325                 330                 335

Cys Ser Cys Arg Phe Pro Glu Glu Glu Glu Gly Gly Cys Glu Leu Arg
                340                 345                 350

Val Lys Phe Ser Arg Ser Ala Asp Ala Pro Ala Tyr Gln Gln Gly Gln
                355                 360                 365

Asn Gln Leu Tyr Asn Glu Leu Asn Leu Gly Arg Arg Glu Glu Tyr Asp
370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
                420                 425                 430

Arg Gly Lys Gly His Asp Gly Leu Tyr Gln Gly Leu Ser Thr Ala Thr
            435                 440                 445

Lys Asp Thr Tyr Asp Ala Leu His Met Gln Ala Leu Pro Pro Arg
450                 455                 460

<210> SEQ ID NO 13
<211> LENGTH: 81
<212> TYPE: DNA
<213> ORGANISM: artificial sequence
<220> FEATURE:
<223> OTHER INFORMATION: 4-1BB transmembrane region

<400> SEQUENCE: 13
atcatctcct tctttcttgc gctgacgtcg actgcgttgc tcttcctgct gttcttcctc      60
acgctccgtt tctctgttgt t                                                81
```

<210> SEQ ID NO 14
<211> LENGTH: 69
<212> TYPE: DNA
<213> ORGANISM: artificial sequence
<220> FEATURE:
<223> OTHER INFORMATION: 4-1BB signal peptide

<400> SEQUENCE: 14
atgggaaaca gctgttacaa catagtagcc actctgttgc tggtcctcaa ctttgagagg    60
acaagatca                                                            69

<210> SEQ ID NO 15
<211> LENGTH: 63
<212> TYPE: DNA
<213> ORGANISM: artificial sequence
<220> FEATURE:
<223> OTHER INFORMATION: CD8a signal peptide

<400> SEQUENCE: 15
atggccttac cagtgaccgc cttgctcctg ccgctggcct tgctgctcca cgccgccagg    60
ccg                                                                  63

<210> SEQ ID NO 16
<211> LENGTH: 144
<212> TYPE: DNA
<213> ORGANISM: artificial sequence
<220> FEATURE:
<223> OTHER INFORMATION: CD8a hinge region

<400> SEQUENCE: 16
gcgaagccca ccacgacgcc agcgccgcga ccaccaacac cggcgcccac catcgcgtcg    60
cagcccctgt ccctgcgccc agaggcgtgc cggccagcgg cggggggcgc agtgcacacg    120
agggggctgg acttcgcctg tgat                                           144

<210> SEQ ID NO 17
<211> LENGTH: 63
<212> TYPE: DNA
<213> ORGANISM: artificial sequence
<220> FEATURE:
<223> OTHER INFORMATION: CD8a transmembrane region

<400> SEQUENCE: 17
atctacatct gggcgccctt ggccgggact tgtggggtcc ttctcctgtc actggttatc    60
acc                                                                  63

<210> SEQ ID NO 18
<211> LENGTH: 126
<212> TYPE: DNA
<213> ORGANISM: artificial sequence
<220> FEATURE:
<223> OTHER INFORMATION: 4-1BB intracellular co-stimulatory signal
      domain

<400> SEQUENCE: 18
aaacggggca gaaagaaact cctgtatata ttcaaacaac catttatgag accagtacaa    60
actactcaag aggaagatgg ctgtagctgc cgatttccag aagaagaaga aggaggatgt    120
gaactg                                                               126

<210> SEQ ID NO 19
<211> LENGTH: 123
<212> TYPE: DNA

<213> ORGANISM: artificial sequence
<220> FEATURE:
<223> OTHER INFORMATION: CD28 intracellular co-stimulatory signal domain

<400> SEQUENCE: 19

| | | | | | |
|---|---|---|---|---|---|
| aggagtaaga | ggagcaggct | cctgcacagt | gactacatga | acatgactcc | cgccgcccc | 60 |
| gggcccaccc | gcaagcatta | ccagccctat | gccccaccac | gcgacttcgc | agcctatcgc | 120 |
| tcc | | | | | | 123 |

<210> SEQ ID NO 20
<211> LENGTH: 339
<212> TYPE: DNA
<213> ORGANISM: artificial sequence
<220> FEATURE:
<223> OTHER INFORMATION: CD3z intracellular signalling domain

<400> SEQUENCE: 20

| | | | | | |
|---|---|---|---|---|---|
| agagtgaagt | tcagcaggag | cgcagacgcc | cccgcgtacc | agcagggcca | gaaccagctc | 60 |
| tataacgagc | tcaatctagg | acgaagagag | gagtacgatg | ttttggacaa | gagacgtggc | 120 |
| cgggaccctg | agatggggg | aaagccgaga | aggaagaacc | ctcaggaagg | cctgtacaat | 180 |
| gaactgcaga | aagataagat | ggcggaggcc | tacagtgaga | ttgggatgaa | aggcgagcgc | 240 |
| cggaggggca | aggggcacga | tggcctttac | cagggtctca | gtacagccac | caaggacacc | 300 |
| tacgacgccc | ttcacatgca | ggccctgccc | cctcgctaa | | | 339 |

<210> SEQ ID NO 21
<211> LENGTH: 777
<212> TYPE: DNA
<213> ORGANISM: artificial sequence
<220> FEATURE:
<223> OTHER INFORMATION: CD19 antigen binding domain

<400> SEQUENCE: 21

| | | | | | |
|---|---|---|---|---|---|
| gaggtgaaac | tgcaggagtc | aggacctggc | ctggtggcgc | cctcacagag | cctgtccgtc | 60 |
| acatgcactg | tctcaggggt | ctcattaccc | gactatggtg | taagctggat | tcgccagcct | 120 |
| ccacgaaagg | gtctggagtg | gctgggagta | atatgggta | gtgaaaccac | atactataat | 180 |
| tcagctctca | aatccagact | gaccatcatc | aaggacaact | ccaagagcca | agttttctta | 240 |
| aaaatgaaca | gtctgcaaac | tgatgacaca | gccatttact | actgtgccaa | acattattac | 300 |
| tacggtggta | gctatgctat | ggactactgg | ggtcaaggaa | cctcagtcac | cgtctcctca | 360 |
| ggcggcggca | gcggcggcgg | cagcggcggc | ggcagcggcg | gcggcagcga | catccagatg | 420 |
| acacagacta | catcctcccct | gtctgcctct | ctgggagaca | gagtcaccat | cagttgcagg | 480 |
| gcaagtcagg | acattagtaa | atatttaaat | tggtatcagc | agaaaccaga | tggaactgtt | 540 |
| aaactcctga | tctaccatac | atcaagatta | cactcaggag | tcccatcaag | gttcagtggc | 600 |
| agtgggtctg | gaacagatta | ttctctcacc | attagcaacc | tggagcaaga | agatattgcc | 660 |
| acttactttt | gccaacaggg | taatacgctt | ccgtacacgt | tcggaggggg | gactaagttg | 720 |
| gaaataacac | gggctgatgc | tgcaccaact | gtatccatct | tcccaccatc | cagtaat | 777 |

<210> SEQ ID NO 22
<211> LENGTH: 1392
<212> TYPE: DNA
<213> ORGANISM: artificial sequence
<220> FEATURE:
<223> OTHER INFORMATION: 4-1BB signal peptide-VH-(G3S)4-VL-4-1BB
    TM-4-1BB cyto-CD3z

<400> SEQUENCE: 22

```
atgggaaaca gctgttacaa catagtagcc actctgttgc tggtcctcaa ctttgagagg      60
acaagatcag aggtgaaact gcaggagtca ggacctggcc tggtggcgcc ctcacagagc     120
ctgtccgtca catgcactgt ctcaggggtc tcattacccg actatggtgt aagctggatt     180
cgccagcctc cacgaaaggg tctggagtgg ctggagtaa tatgggtag tgaaaccaca       240
tactataatt cagctctcaa atccagactg accatcatca aggacaactc caagagccaa    300
gttttcttaa aaatgaacag tctgcaaact gatgacacag ccatttacta ctgtgccaaa    360
cattattact acggtggtag ctatgctatg gactactggg gtcaaggaac ctcagtcacc    420
gtctcctcag gcggcggcag cggcggcggc agcggcggcg gcagcggcgg cggcagcgac    480
atccagatga cacagactac atcctccctg tctgcctctc tgggagacag agtcaccatc    540
agttgcaggg caagtcagga cattagtaaa tatttaaatt ggtatcagca gaaaccagat    600
ggaactgtta aactcctgat ctaccataca tcaagattac actcaggagt cccatcaagg    660
ttcagtggca gtgggtctgg aacagattat tctctcacca ttagcaacct ggagcaagaa    720
gatattgcca cttactttg ccaacagggt aatacgcttc cgtacacgtt cggaggggg      780
actaagttgg aaataaacg ggctgatgct gcaccaacta tatccatctt cccaccatcc     840
agtaatatca tctccttctt tcttgcgctg acgtcgactg cgttgctctt cctgctgttc    900
ttcctcacgc tccgtttctc tgttgttaaa cggggcagaa agaaactcct gtatatattc    960
aaacaaccat ttatgagacc agtacaaact actcaagagg aagatggctg tagctgccga   1020
tttccagaag aagaagaagg aggatgtgaa ctgagagtga agttcagcag gagcgcagac   1080
gccccgcgt accagcaggg ccagaaccag ctctataacg agctcaatct aggacgaaga    1140
gaggagtacg atgttttgga caagagacgt ggccgggacc ctgagatggg gggaaagccg   1200
agaaggaaga accctcagga aggcctgtac aatgaactgc agaaagataa gatggcggag   1260
gcctacagtg agattgggat gaaaggcgag cgccggaggg gcaaggggca cgatggcctt   1320
taccagggtc tcagtacagc caccaaggac acctacgacg cccttcacat gcaggccctg   1380
cccctcgct aa                                                         1392
```

<210> SEQ ID NO 23
<211> LENGTH: 1512
<212> TYPE: DNA
<213> ORGANISM: artificial sequence
<220> FEATURE:
<223> OTHER INFORMATION: CD8a signal peptide-VH-(G3S)4-VL-CD8a hinge
    TM-4-1BB cyto-CD3z

<400> SEQUENCE: 23

```
atggccttac cagtgaccgc cttgctcctg ccgctggcct tgctgctcca cgccgccagg      60
ccggaggtga aactgcagga gtcaggacct ggcctggtgg cgccctcaca gagcctgtcc     120
gtcacatgca ctgtctcagg gtctcatta cccgactatg gtgtaagctg gattcgccag     180
cctccacgaa agggtctgga gtggctggga gtaatatggg gtagtgaaac cacatactat    240
aattcagctc tcaaatccag actgaccatc atcaaggaca actccaagag ccaagttttc    300
ttaaaaatga cagtctgca aactgatgac acagccattt actactgtgc caaacattat    360
tactacggtg gtagctatgc tatggactac tggggtcaag gaacctcagt caccgtctcc    420
tcaggcggcg gcagcggcgg cggcagcggc ggcagcg gcggcggcag cgacatccag        480
atgacacaga ctacatcctc cctgtctgcc tctctgggag acagagtcac catcagttgc    540
```

| | |
|---|---|
| agggcaagtc aggacattag taaatattta aattggtatc agcagaaacc agatggaact | 600 |
| gttaaactcc tgatctacca tacatcaaga ttacactcag gagtcccatc aaggttcagt | 660 |
| ggcagtgggt ctggaacaga ttattctctc accattagca acctggagca agaagatatt | 720 |
| gccacttact tttgccaaca gggtaatacg cttccgtaca cgttcggagg ggggactaag | 780 |
| ttggaaataa cacgggctga tgctgcacca actgtatcca tcttcccacc atccagtaat | 840 |
| gcgaagccca ccacgacgcc agcgccgcga ccaccaacac cggcgcccac catcgcgtcg | 900 |
| cagcccctgt ccctgcgccc agaggcgtgc cggccagcgg cggggggcgc agtgcacacg | 960 |
| agggggctgg acttcgcctg tgatatctac atctgggcgc ccttggccgg gacttgtggg | 1020 |
| gtccttctcc tgtcactggt tatcaccaaa cggggcagaa agaaactcct gtatatattc | 1080 |
| aaacaaccat ttatgagacc agtacaaact actcaagagg aagatggctg tagctgccga | 1140 |
| tttccagaag aagaagaagg aggatgtgaa ctgagagtga agttcagcag gagcgcagac | 1200 |
| gcccccgcgt accagcaggg ccagaaccag ctctataacg agctcaatct aggacgaaga | 1260 |
| gaggagtacg atgttttgga caagagacgt ggccgggacc ctgagatggg gggaaagccg | 1320 |
| agaaggaaga accctcagga aggcctgtac aatgaactgc agaaagataa gatggcggag | 1380 |
| gcctacagtg agattgggat gaaaggcgag cgccggaggg gcaaggggca cgatggcctt | 1440 |
| taccagggtc tcagtacagc caccaaggac acctacgacg cccttcacat gcaggccctg | 1500 |
| ccccctcgct aa | 1512 |

<210> SEQ ID NO 24
<211> LENGTH: 1392
<212> TYPE: DNA
<213> ORGANISM: artificial sequence
<220> FEATURE:
<223> OTHER INFORMATION: CD8a signal peptide-VH-(G3S)4-VL-4-1BB TM-4-1BB cyto-CD3z
<400> SEQUENCE: 24

| | |
|---|---|
| atggctctgc ctgtcaccgc tctgctgctg cccctggctc tgctgctgca cgccgcaaga | 60 |
| cctgaagtca aactgcagga atctggccca ggcctggtgg cacctagcca gtccctgtct | 120 |
| gtgacctgca cagtgagcgg cgtgtccctg cctgactacg gcgtgtcttg gatcagacag | 180 |
| ccacctagga agggcctgga gtggctggga gtgatctggg gctccgagac aacatactat | 240 |
| aactctgccc tgaagagccg cctgaccatc atcaaggata cagcaagtc ccaggtgttc | 300 |
| ctgaagatga atagcctgca gaccgacgat acagccatct actattgcgc caagcactac | 360 |
| tattacggcg gcagctatgc catggactac tggggccagg gcacctccgt gacagtgagc | 420 |
| tccggaggag gctccggagg aggctctgga ggcggcagcg gcggcggctc cgatatccag | 480 |
| atgacccaga cccacatctag cctgtctgca agcctgggcg accgcgtgac aatctcttgt | 540 |
| cgggccagcc aggatatctc caagtatctg aattggtacc agcagaagcc gacggcacc | 600 |
| gtgaagctgc tgatctatca caccagccgg ctgcacagcg gagtgccttc aggttctccc | 660 |
| ggctctggca gcggaaccga ctactctctg acaatcagca cctggagca ggaggatatc | 720 |
| gccacctatt tctgccagca gggcaatacc ctgccttaca catttggcgg cggcaccaag | 780 |
| ctggagatca agagaccga tgccgcccca acagtgagca tctttccacc ctcctctaac | 840 |
| actagtatca tctccttctt tctggcctg acctctacag ccctgctgtt cctgctgttc | 900 |
| tttctgaccc tgaggtttc cgtggtgaag agaggcagga gaagctgct gtacatcttc | 960 |
| aagcagcctt ttatgcgccc agtgcagacc acacaggagg aggacggctg ctcttgtcgg | 1020 |

-continued

```
ttcccagagg aggaggaggg cggctgtgag ctgagagtga agttttccag gtctgcagat   1080
gcaccagcat atcagcaggg acagaatcag ctgtacaacg agctgaatct gggccggaga   1140
gaggagtatg acgtgctgga taagaggagg ggacgggacc ccgagatggg aggcaagcca   1200
cggagaaaga accccagga gggcctgtat aatgagctgc agaaggacaa gatggccgag   1260
gcctactccg agatcggcat gaagggagag aggaggaggg gaaagggaca cgatggcctg   1320
taccagggcc tgagcaccgc aacaaaagac acttatgacg cactgcacat gcaggctctg   1380
cccccaaggt aa                                                       1392
```

CHIMERIC ANTIGEN RECEPTOR AND USE THEREOF

CROSS-REFERENCE TO RELATED APPLICATION

This application is a Section 371 of International Application No. PCT/CN2017/119711, filed Dec. 29, 2017, which was published in the Chinese language on Jul. 5, 2018, under International Publication No. WO 2018/121712 A1, which claims priority under 35 U.S.C. § 119(b) to Chinese Application No. 201611263835.1, filed Dec. 30, 2016. Each disclosure is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "689316.3US Sequence Listing" having a creation date of Jun. 28, 2019 and having a size of 28 kb. The sequence listing submitted via EFS-Web is part of the specification and is herein incorporated by reference in its entirety.

TECHNICAL FIELD

The present invention belongs to the technical field of biomedicine or biopharmaceutics, and relates to a novel chimeric antigen receptor and use thereof.

BACKGROUND ART

According to the 2015 Global Cancer Statistics, data showed that in 2012, there were 14.1 million new tumor patients and 8.2 million patients died worldwide. According to the Chinese Cancer Registry, data showed that in 2015, there were 4.3 million new cancer cases in China, and more than 2.81 million cancer patients died, accounting for 28.82% of the total number of deaths in the year, that is, an average of more than 7,500 people died of cancer every day, which was ranked number one in the world.

Traditional tumor treatment means mainly comprise surgery, radiotherapy, chemotherapy, and stem cell transplant arising in recent years. These treatment means often cure the symptoms, not the underlying problems. With the development of science, immunotherapy of tumor has achieved a great breakthrough in recent years, which mainly comprises immunological checkpoint inhibitors (such as anti-PD1 monoclonal antibody), and chimeric antigen receptor modified T cell therapy (CAR-T) with the best clinical effect. In recent years, CAR-T technology has made encouraging progresses in clinical trials of hematologic disease treatment, and was ranked as number one of top ten scientific breakthroughs in 2013 by *Science* magazine. Since the CAR1 June group in University of Pennsylvania firstly reported in 2013 that the child (Emily Whitehead) suffering from the acute B lymphoblastic leukemia who was treated with the targeted CD19 CAR-T was completely relieved, the CAR-T cell immunotherapy had rapidly developed in just a few years. Currently, CAR-T cell treatment is the most effective cell immunotherapy with the highest targeting ability. After the evolution of technology, CAR-T has become more sensitive and more immune persistent, and has a miraculous effect on hematologic tumors such as lymphoma. At present, a number of cell treatment methods have been awarded the "breakthrough therapy" qualification by the FDA. Among them, the results of a number of clinical trials have shown that the clinical complete remission rate of CD19 CAR-T treatment of B-cell lymphoma has exceeded 90%.

CAR-T cells are a class of T cells that can be genetically engineered to express CAR recognizing particular antigens on the T cell surface and transmit signals. Generally, CAR-T cells recognize specific molecules on the tumor cell surface via a chimeric antigen receptor (CAR) in an antigen-antibody or ligand-receptor recognition mode, and then are activated and proliferated and exert cell killing function through the intracellular signal transduction. The chimeric antigen receptor modified T cells can specifically recognize tumor-associated antigens, making the targeting ability, killing activity and persistence of effector T cells higher than those of conventionally used immune cells, and can overcome local immunosuppression microenvironment of tumors and break the host's immune tolerance state.

The modified T cells express such a class of chimeric antigen receptor molecules composed of: an extracellular segment generally comprising a CD8α or GM-CSFRα signal peptide, an antigen recognition region, or an antigen binding domain comprising a single chain variable region consisting of heavy chain and light chain variable regions of an antibody; an intracellular segment which is an intracellular chimera of various signalling molecules including CD28, 4-1BB, OX-40, CD3zeta, etc.; and a transmembrane region which is derived from other molecules, such as PD1, CD8, CD4, CD28, CD3zeta (CD3ζ), etc. The non-antigen recognition region of the extracellular segment of CAR comprises a signal peptide and a hinge region (a linking region between the scFv and the transmembrane region, also referred to as a spacer domain), and has an important influence on the function of the CAR. Kober L et al. in Germany reported that the expression level of a bi-specific single chain antibody (bi-specific scFv antibody) can be significantly increased by optimizing the signal peptide sequence pair from different sources, which is closely related to the ability of the signal peptide to guide the protein into the secretory pathway (Biotechnol Bioeng. 2013 April; 110(4): 1164-73). Michael Hudecek et al. in the Fred Hutchinson Cancer Research Center in the United States reported that although the CAR using an inappropriate spacer domain has a good tumor cell killing effect in in vitro experiments, the CAR-T cells undergo activation-induced T cell death in vivo due to the binding of the spacer domain to the Fc receptor, resulting in the inability of such CAR constructs to persist in vivo and loss of anti-tumor activity (Cancer Immunol Res; 3(2); 125-35). In the international application WO 2016/014789 A2, without changing the extracellular antigen recognition region and the intracellular signal region, the performance of the CAR vector can be greatly realized by only changing the sequence of the transmembrane region, and the non-specific killing effect of the CAR-T on the non-target cells is reduced. Currently, in the field of CAR-T, compared with the CD28 intracellular signal domain, the CAR structure containing a 4-1BB intracellular signal domain is considered to have better tumor cell killing activity and persistence in vivo.

In the field of B cell leukemia, CD19 is expressed on the surfaces of almostly all the B cell tumor cells, but is hardly expressed in other parenchymal cells and hematopoietic stem cells. CD19 is a relatively specific B-line tumor antigen target. The CD19 CAR structure that has achieved a significant clinical progress at present is CD8α signal peptide-anti-CD19 single chain antibody-CD8α hinge region & transmembrane region-4-1BB intracellular region-CD3ζ intracellular region (CD8α signal peptide-antiCD19scFv-CD8α Hinge&TM-4-1BBcyto-CD3ζ).

Human 4-1BB molecule (NCBI database protein number NP_001552.2), also known as CD137, or tumor necrosis factor receptor superfamily member 9 (TNFRSF9), has amino acids 1-23 as a signal peptide, amino acids 24-186 as an extracellular region, amino acids 187-213 as a transmembrane region, and amino acids 214-255 as an intracellular region in its primary structure. At present, there is no report that designs a CAR using the basic structure of 4-1BB.

The present invention provides a novel CAR structure comprising a 4-1BB signal peptide and/or a 4-1BB transmembrane region structure, for example, a 4-1BB signal peptide-tumor antigen recognition binding region-4-1BB transmembrane region-4-1BB intracellular region-CD3zeta intracellular region (4-1BB signal peptide-VH-Linker-VL/VHH-4-1BB TM-4-1BBcyto-CD3ζ), which maximizes the use of the amino acid sequence of 4-1BB. The use of the 4-1BB signal peptide, and the transmembrane region and intracellular region of 4-1BB facilitates the optimization of the extension of the extracellular tumor antigen recognition binding region on CAR-T cells, which not only achieves good tumor killing effects in vitro and in vivo, but also achieves complete remission in the clinical treatment of patients with acute lymphoma, with a milder cytokine release response.

SUMMARY OF THE INVENTION

The object of the present invention is to provide a novel chimeric antigen receptor and use thereof in view of the above-mentioned deficiencies of the prior art.

Another object of the present invention is to provide a nucleic acid encoding the chimeric antigen receptor.

Still another object of the present invention is to provide a cell containing the chimeric antigen receptor and use thereof.

Provided is a novel chimeric antigen receptor, comprising an extracellular signal peptide, an antigen binding domain, a transmembrane domain and an intracellular signal domain, wherein said extracellular signal peptide is selected from one of a 4-1BB signal peptide, a CD8α signal peptide, a GM-CSFRα signal peptide or a CD4 signal peptide, and the transmembrane domain is selected from a 4-1BB molecular transmembrane region sequence.

The amino acid sequence of a 4-1BB molecular transmembrane region as said transmembrane domain is preferably as set forth in SEQ ID NO. 1, or a polypeptide having 85%-99% identity with the amino acid sequence of SEQ ID NO. 1.

Said extracellular signal peptide is preferably a 4-1BB signal peptide with an amino acid sequence as set forth in SEQ ID NO. 2, or a polypeptide having 85%-99% identity with the amino acid sequence of SEQ ID NO. 2.

An antigen bound by said antigen binding domain is associated with a malignant tumor, and includes but not limited to CD19, CD20, CD22, CD30, CD33, CD38, BCMA, CS1, CD138, CD123/IL3Rα, c-Met, gp100, MUC1, IGF-I receptor, EPCAM, EGFR/EGFRvIII, HER2, PD1, CTLA4, IGF1R, mesothelin, PSMA, WT1, ROR1, CEA, GD-2, NY-ESO-1, MAGE A3, GPC3, glycolipid F77 or any other tumor antigen or other modified types or a combination thereof.

The antigen bound by said antigen binding domain is further preferably CD19; the amino acid sequence of the CD19 antigen binding domain is as set forth in SEQ ID NO. 9.

In one embodiment, the antigen binding domain of said chimeric antigen receptor binds to a target by a ligand-receptor interaction and may be selected from IL-3, IL-13 or APRIL.

Said antigen binding domain consists of antibody fragments, preferably monoclonal antibodies, Fab, scFv, sdAb, $V_HH$ or other antibody fragments. The antibody from which the antigen binding domain is derived can be derived from a murine antibody, a camel antibody or a humanized antibody. In one specific example, the antigen binding domain of the chimeric antigen receptor consists of a CD19-specific single chain antibody fragment, containing a heavy chain variable region (VH) and a light chain variable region (VL) of a single chain antibody.

In one embodiment, the heavy chain variable region (VH) and the light chain variable region (VL) of the single chain antibody of said antigen binding domain are linked by a connecting peptide (linker), comprising a GS linker such as $(G_3S)_4$, $(G_4S)_3$ or GSTSGSGKPGSGEGSTKG, preferably $(G_3S)_4$ connecting peptide.

Said intracellular signal domain preferably comprises an intracellular signal region sequence of CD3 zeta (CD3ζ), CD3 gamma, CD3 delta, CD3 epsilon, common FcR gamma (FCER1G), FcR beta (Fc Epsilon R1b), CD79a, CD79b, Fc gamma RIIa, DAP10 and DAP12 molecules, or a combination thereof. Further preferably, the intracellular signal domain comprises a signalling domain of a CD3ζ molecule.

Said intracellular signal domain preferably also comprises a co-stimulatory signal domain, which may be selected from the following co-stimulatory signal molecules: CD27, CD28, 4-1BB, OX40, CD30, CD40, CD2, lymphocyte function-associated antigen-1 (LFA-1), LIGHT, NKG2C, B7-H3, PD-1, ICOS, CDS, ICAM-1, GITR, BAFFR, HVEM (LIGHTR), SLAMF7, CD7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, NKp44, NKp30, NKp46, NKG2D, a ligand specifically binding to CD83, or any combination thereof. In one specific embodiment, further preferably, the 4-1BB is a co-stimulatory signal domain, the amino acid sequence of which is as set forth in SEQ ID NO. 6.

In one embodiment, the chimeric antigen receptor does not comprise a hinge region between the extracellular antigen binding domain and the transmembrane domain.

In another embodiment, the chimeric antigen receptor comprises a hinge region between the extracellular antigen binding domain and the transmembrane domain. In a specific embodiment, the hinge region is preferably the CD8α hinge region as set forth in SEQ ID NO. 4.

In a particular embodiment, the chimeric antigen receptor preferably comprises a 4-1BB signal peptide or CD8α signal peptide, an antigen binding domain, a 4-1BB transmembrane region, a 4-1BB intracellular co-stimulatory domain, and a CD3ζ signalling domain which are sequentially connected.

The structure of the chimeric antigen receptor of the present invention is as follows:

4-1BB signal peptide-VH-Linker-VL-4-1BB TM-4-1BBcyto-CD3ζ

CD8α signal peptide-VH-Linker-VL-4-1BB TM-4-1BBcyto-CD3ζ

4-1BB signal peptide-VH-Linker-VL-TM-4-1BBcyto-CD3ζ

4-1BB signal peptide-$V_HH_1$-Linker-$V_HH_2$-4-1BB TM-4-1BBcyto-CD3ζ

CD8α signal peptide-$V_HH_1$-Linker-$V_HH_2$-4-1BB TM-4-1BBcyto-CD3ζ

4-1BB signal peptide-$V_HH_1$-Linker-$V_HH_2$-TM-4-1BBcyto-CD3ζ wherein the antigen binding domain may consist of VH-Linker-VL or VL-Linker-VH or $V_HH_1$-Linker-$V_HH_2$, and $V_HH_1$ and $V_HH_2$ can recognize the same antigen or different antigens.

As a preferable embodiment of the present invention, the chimeric antigen receptor comprises an amino acid sequence as set forth in SEQ ID NO. 10 or SEQ ID NO. 12, or an amino acid sequence having 85%-99% identity with SEQ ID NO. 10 or SEQ ID NO. 12.

A nucleic acid molecule encoding the aforementioned chimeric antigen receptor is provided.

The nucleic acid molecule preferably comprises a nucleotide sequence of SEQ ID NO. 22 or SEQ ID NO. 24.

An expression vector of the above-mentioned nucleic acid molecule is provided.

The expression vector is preferably a lentivirus expression vector, which comprises a nucleotide sequence encoding SEQ ID NO. 22 or SEQ ID NO. 24.

A cell expressing the aforementioned chimeric antigen receptor is provided.

The cell is preferably an immune cell, further preferably, T lymphocyte, NK cell, an immune cell differentiated by culturing a hematopoietic stem cell, a pluripotent stem cell or an embryonic stem cell.

A method for preparing a T cell modified by the novel chimeric antigen receptor is provided, the method comprising separating and activating the T cell to be modified, and then transducing the T cell with the aforementioned expression vector.

The use of said novel chimeric antigen receptor, said expression vector, and said cell in the preparation of a medicament for treating a tumor is provided.

Said tumor preferably comprises glioblastoma, head and neck cancer, thyroid cancer, kidney cancer, lung cancer, breast cancer or ovarian cancer, and chronic lymphoblastic leukemia (CLL), acute leukemia, acute lymphoblastic leukemia (ALL), B-cell acute lymphoblastic leukemia (ALL), T-cell acute lymphoblastic leukemia (T-ALL), chronic myeloid leukemia (CML), B-cell prolymphocytic leukemia, acute plasmacytoid dendritic cell tumor, Burkitt lymphoma, diffuse large B-cell lymphoma, follicular lymphoma hairy cell leukemia, small cell or large cell follicular lymphoma, malignant lymphoid tissue hyperplasia, MALT lymphoma, mantle cell lymphoma, marginal zone lymphoma, multiple myeloma, myeloproliferative disorder and myelodysplastic syndrome, non-Hodgkin's lymphoma, Hodgkin's lymphoma, plasmablastic lymphoma, plasmacytoid dendritic cell tumor lymphoma and other hematologic tumors.

In a specific embodiment, the invention relates to the use in the preparation of a medicament for treating a hematologic tumor.

The present invention relates to the use of the novel chimeric antigen receptor in the preparation of an anti-tumor drug and in cell immunotherapy.

The present invention relates to the use of the immune effector cells in the preparation of an anti-tumor drug and in cell immunotherapy.

BENEFICIAL EFFECTS

The present invention provides a novel CAR structure comprising a 4-1BB signal peptide and/or a 4-1BB transmembrane region structure, for example, a 4-1BB signal peptide-tumor antigen recognition binding region-4-1BB transmembrane region-4-1BB intracellular region-CD3zeta intracellular region (4-1BB signal peptide-VH-Linker-VL/VHH-4-1BB TM-4-1BBcyto-CD3ζ), which maximizes the use of the amino acid sequence of 4-1BB molecular structure. The use of the 4-1BB signal peptide, and the transmembrane region or intracellular region structures of 4-1BB facilitates the extension of the extracellular tumor antigen recognition binding region on CAR-T cells, which not only achieves good tumor killing effects in vitro and in vivo, but also achieves complete remission in the clinical treatment of patients with acute lymphoma, with a milder cytokine release response. Taking the CD19 antigen target as an example, the novel chimeric antigen receptor shows a relatively higher anti-tumor ability compared with the prior art, and immune cells modified by the chimeric antigen receptor have a higher ability to target and recognize tumor antigens, thereby enhancing the killing activity against tumor cells.

DETAILED DESCRIPTION OF EMBODIMENTS

Figure 1:
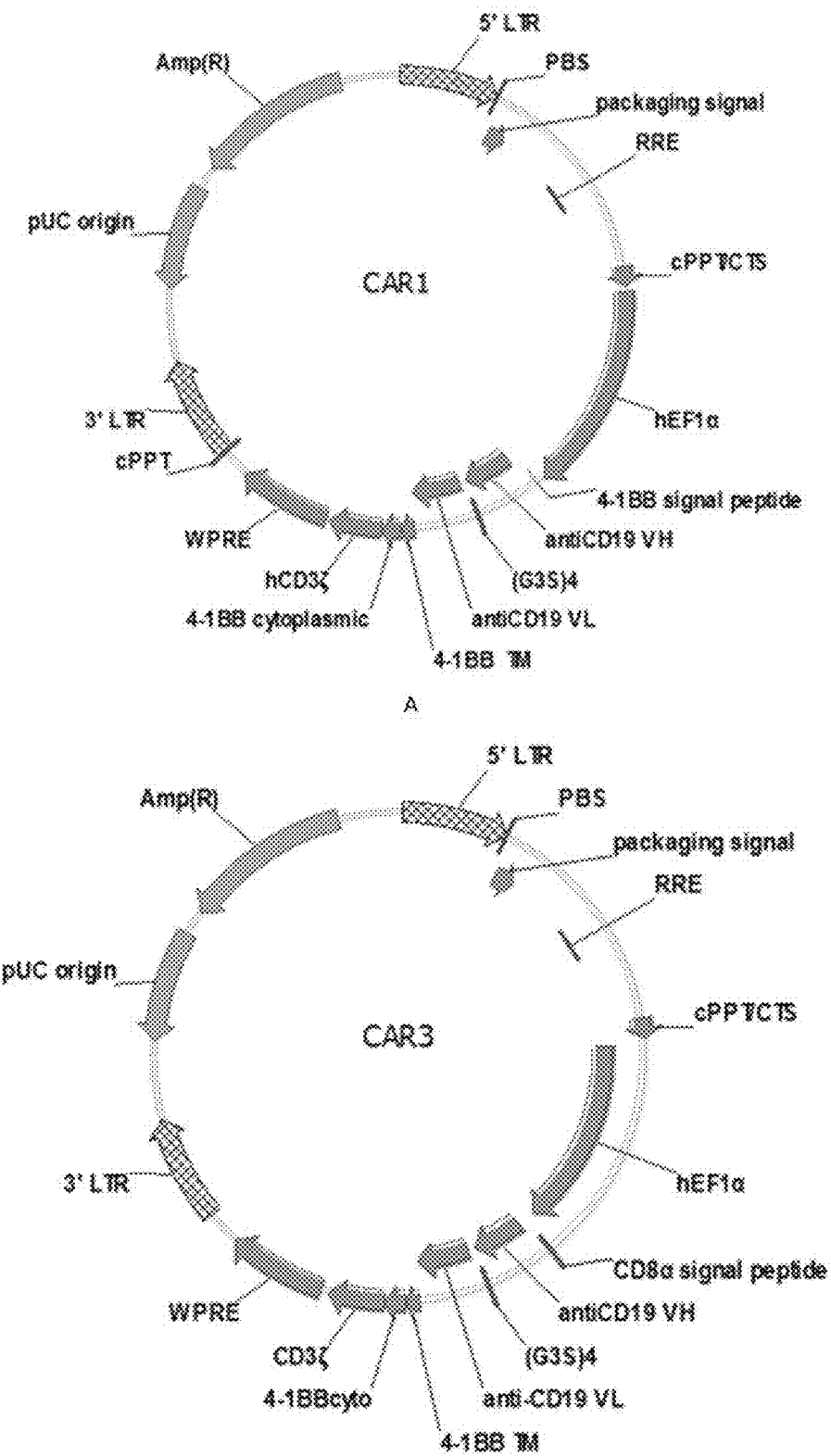
FIG. 1 is a vector structure graph for a chimeric antigen receptor, showing the structure of the vectors for the CAR1 (panel A) and CAR3 (panel B) chimeric antigen receptors in the present invention.

The present invention provides a novel chimeric antigen receptor, immune effector cells and their use in inhibiting tumor activity. The present invention is further illustrated in conjunction with the following specific examples.

The term "transmembrane domain" (abbreviated as TM) as used herein may be used interchangeably with "transmembrane region" and refers to a protein structure region which has thermodynamical stability and is anchored within the cell membrane. The transmembrane region can be obtained from a native protein selected from the 4-1BB molecule.

The novel chimeric antigen receptor of the present invention comprises an extracellular signal peptide structure, such as a 4-1BB signal peptide, a CD8α signal peptide, a GM-CSFRα signal peptide or a CD4 signal peptide, preferably a 4-1BB signal peptide.

The term "intracellular signal domain" as used herein refers to a protein structure region that is capable of transducing the cell effector function signal and directing the cell to perform a particular function. The intracellular signal domain can comprise a signalling domain and/or a co-stimulatory signal domain.

As used herein, the term "identity" of amino acid sequences can be used interchangeably with "similarity" to refer to the degree of similarity between amino acid sequences determined by a sequence alignment software such as BLAST. Methods and software for alignment of amino acid sequences are well known to those skilled in the art. A modified amino acid sequence can be obtained by making substitutions, deletions, and/or additions of one or more (e.g., 1-15, such as, 2, 3, 5, 8, 10 or 12) amino acid residues on the basis of a known amino acid sequence. For example, a variant sequence having at least 85% (e.g., 85%-99% or 90%-99% or 95%-99%) sequence identity with SEQ ID NO. 1 and having a substantially same transmembrane function can be obtained by modifying the 4-1BB transmembrane domain as set forth in SEQ ID NO. 1 of the present invention through conventional protein engineering means (e.g., conservative substitution of amino acids, etc.).

The term "antibody fragment" as used herein is a portion of an antibody having functions, preferably a variable region for antigen binding and/or a variable region of an intact antibody. Antibody fragments comprise Fab, Fab', F(ab')$_2$, Fv fragments, single chain antibody scFv, single domain antibody sdAb/V$_H$H and multispecific antibodies.

The term "scFv" or "scFv antibody" as used herein refers to a single chain antibody fragment (scFv) which is formed by connecting a heavy chain variable region VH and a light chain variable region VL of an antibody with a short peptide of 15-20 amino acids. As used herein, the term "Linker", also referred to as a connecting peptide or adapter, refers to a flexible amino acid sequence used to connect two domains. Selection and preparation of a connecting peptide is readily available to those skilled in the art.

The present invention designs a chimeric antigen receptor using the human 4-1BB molecular domain through optimization and is further illustrated in conjunction with the following specific examples.

Example 1 Preparation of a Chimeric Antigen Receptor (I) Preparation of the Gene Fragment of a Chimeric Antigen Receptor The present invention provides a novel chimeric antigen receptor comprising a CD19 antigen binding domain. The antibody from which the antigen binding domain is derived, provided by the present invention, consists of a heavy chain variable region (VH), a light chain variable region (VL) of a single chain antibody and a connecting peptide (G3S)$_4$ Linker. The heavy chain variable region and the light chain variable region sequence of the single chain antibody were derived from GenBank:Y14283.1 and GenBank:Y14284.1, respectively. Their codons and sequences were optimized to ensure that they were more suitable for expression in human cells.

The novel chimeric antigen receptor provided by the present invention can be designed according to the order of the following coding genes and the fusion gene fragments for the chimeric antigen receptor can be changed: the 4-1BB signal peptide, $V_H$-(G3S)$_4$-$V_L$, the 4-1BB transmembrane region, the 4-1BB or CD28 intracellular co-stimulatory signal domain or the CD3ζ intracellular signalling domain. The gene synthesis technology service was provided by Nanjing Genscript Biotechnology Co., Ltd. The following coding gene sequences were selected by gene synthesis technology to perform the fusion gene synthesis:

the nucleotide sequence encoding the 4-1BB transmembrane region as set forth in SEQ ID NO. 13;
the nucleotide sequence encoding the 4-1BB signal peptide as set forth in SEQ ID NO. 14;
the nucleotide sequence encoding the CD8α signal peptide as set forth in SEQ ID NO. 15;
the nucleotide sequence encoding the CD8α hinge region as set forth in SEQ ID NO. 16;
the nucleotide sequence encoding the CD8α transmembrane region as set forth in SEQ ID NO. 17;
the nucleotide sequence encoding the 4-1BB intracellular co-stimulatory signal domain as set forth in SEQ ID NO. 18;
the nucleotide sequence encoding the CD28 intracellular co-stimulatory signal domain as set forth in SEQ ID NO. 19;
the nucleotide sequence encoding the CD3ζ intracellular signalling domain as set forth in SEQ ID NO. 20; and
the nucleotide sequence encoding the CD19 antigen binding domain as set forth in SEQ ID NO. 21.

The extracellular domain and the intracellular signal domain used in the present invention have various combinations, and comprise the structures or combinations selected from the following items:

the 4-1BB transmembrane region having an amino acid sequence as set forth in SEQ ID NO. 1;
the 4-1BB signal peptide having an amino acid sequence as set forth in SEQ ID NO. 2;

the CD8α signal peptide having an amino acid sequence as set forth in SEQ ID NO. 3;

the CD8α hinge region having an amino acid sequence as set forth in SEQ ID NO. 4;

the CD8α transmembrane region having an amino acid sequence as set forth in SEQ ID NO. 5;

the 4-1BB intracellular co-stimulatory signal domain having an amino acid sequence as set forth in SEQ ID NO. 6;

CD28 intracellular co-stimulatory signal domain having an amino acid sequence as set forth in SEQ ID NO. 7;

the CD3ζ intracellular signalling domain having an amino acid sequence as set forth in SEQ ID NO. 8; and the CD19 antigen binding domain having an amino acid sequence as set forth in SEQ ID NO. 9.

The composition of the chimeric antigen receptor in the examples of the present invention include, but not limited to, the following structures:

CAR1: 4-1BB signal peptide-$V_H$-(G3S)$_4$-VL-4-1BB TM-4-1BBcyto-CD3ζ, the amino acid sequence of which is as set forth in SEQ ID NO. 10 and the nucleotide coding sequence of which is as set forth in SEQ ID NO. 22; the gene sequence as set forth in SEQ ID NO. 22 was synthesized to construct a recombinant expression vector;

CAR2: CD8α signal peptide-$V_H$-(G3S)$_4$-$V_L$-CD8α Hinge&TM-4-1BBcyto-CD3ζ, the amino acid sequence of which is as set forth in SEQ ID NO. 11 and the nucleotide coding sequence of which is as set forth in SEQ ID NO. 23; the gene sequence as set forth in SEQ ID NO. 23 was synthesized to construct a recombinant expression vector;

CAR3: CD8α signal peptide-$V_H$-(G3S)$_4$-$V_L$-4-1BB TM-4-1BBcyto-CD3ζ, the amino acid sequence of which is as set forth in SEQ ID NO. 12, and the nucleotide coding sequence of which is as set forth in SEQ ID NO. 24; the gene sequence as set forth in SEQ ID NO. 24 was synthesized to construct a recombinant expression vector;

wherein the antigen binding domain can be replaced with different tumor antigen targets within the technical scope of the art. The antigen-specific heavy chain variable region and light chain variable region of the antibody can be linked in the direction of $V_H$-$V_L$ or $V_L$-$V_H$, and the connecting peptide Linker can be selected from (G3S)$_4$Linker, (G4S)$_3$Linker or other GS Linker or other protein linkers, such as Whitlow Linker: GSTSGSGKPGSGEGSTKG.

(II) Construction of a Lentivirus Expression Vector for a Chimeric Antigen Receptor In one specific embodiment, the present invention uses a self-inactivated lentivirus expression vector to express the target CAR gene sequence. First, the expression plasmid and pCMV-ΔR-8.74 and pMD2.G helper plasmid were extracted and mixed in a certain ratio to co-transfect 293T cells. After transfection for 48 h and 96 h, the cell culture supernatant containing the virus was collected and centrifuged at 3000 rpm at 4° C. for 5 min. After the supernatant was filtered through a 0.45 μm filter, it was mixed with PEG6000/NaCl in a volume ratio of 4:1, and allowed to stand at 4° C. for 2-3 h, and then centrifuged at a high speed for 30 min. The supernatant was discarded, and the pellet was resuspended and dissolved in pre-cooled PBS to obtain a virus concentrate which was stored at −80° C. until use.

Example 2 Construction of the K562 Cell Line Expressing CD19 Antigen (K562.CD19.Luc)

K562 cells hardly express CD19. For the gene synthesis of the nucleotide sequence encoding human CD19 molecule (the protein sequence thereof is NCBI number NP_001171569.1) in the present invention, the gene synthesis technology service was provided by Nanjing Genscript Biotechnology Co., Ltd. Under the action of T4 ligase, the synthesized CD19 nucleotide sequence was ligated at 20° C. overnight to the pLVX-Puro (Clontech, Cat #632164) lentivirus vector which was digested at the BamH1 and XbaI restriction sites in advance. The ligation product was transformed into DH5α competent cells and plated onto bacterial plates, and multiple clone spots were picked for the extraction of plasmids (Qiagen Endofree Mega kit). After enzyme digestion identification, sequencing and alignment, the successfully constructed vector was named as pLVX-CD19-Puro.

The extracted pLVX-CD19-Puro expression plasmid and pCMV-ΔR-8.74 (J. Virol.-1998-Dull-A third-generation lentivirus vector with a conditional packaging system) and pMD2.G helper plasmid were mixed in a certain ratio to co-transfect 293FT cells. After transfection for 96 h, the cell culture supernatant containing the virus was collected and centrifuged at 3000 rpm at 4° C. for 5 min. After the supernatant was filtered through a 0.45 μm filter, it was centrifuged at a high speed of 25,000 rpm at 4° C. for 120 min. The virus concentrate was obtained after discarding the supernatant and resuspending the pellets to dissolve, and stored at −80° C. until use. The lentivirus vector carrying the firefly luciferase/Luciferase reporter gene was also prepared by the same method.

The K562 cell line was purchased from ATCC (Cat No. CCL-243), and was subjected to conventional culture using 90% IMDM (Life technology, Cat No. A10491-01)+10% FBS (Life technology, Cat #10099-141)+1% penicillin/streptomycin (Life technology, Cat #15140-122) (hereinafter referred to as IMDM10 culture solution in short). The constructed lentivirus vector carrying the CD19 gene and the lentivirus vector carrying the firefly luciferase/Luciferase reporter gene were added to the cultured K562 cell supernatant to co-transduce the K562 cell line. After transduction for 24 h, puromycin was added at a final concentration of 10 μg/ml. The culture solution was exchanged every three days and puromycin at the same concentration was added. The screening of monoclones were further performed to obtain monoclonal cells, which were named as K562.CD19.Luc. Another stable cell line K562.CD123.Luc (CD123 gene source: GenBank:NM_002183) constructed simultaneously according to the above-mentioned method in the present invention was used as a CD19 negative control cell line.

The CD19-positive human lymphoma cell line Raji was purchased from American ATCC (ATCC #CCL86™) and was cultured with RPMI1640+10% FBS+1% penicillin/streptomycin (hereinafter referred to as R10 culture solution in short). The firefly luciferase/Luciferase reporter gene was transduced into Raji cells using a method similar to the above-mentioned method. A cell line stably expressing the luciferase reporter gene was obtained by the screening under the puromycin stress, which was named as Raji.Luc.

Figure 2:
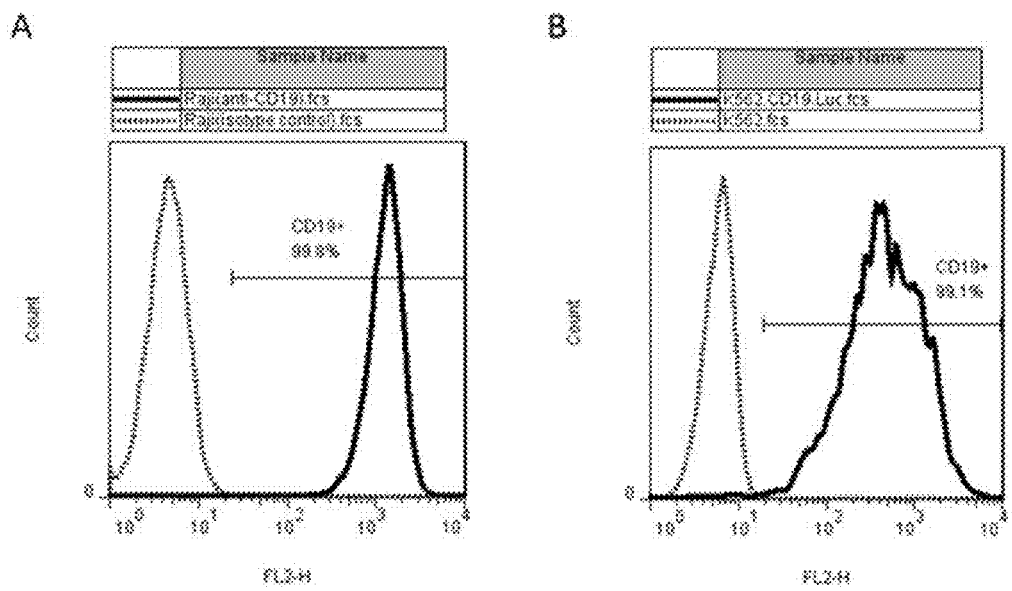
FIG. 2 shows the detection of CD19 antigen expressed by a stable cell line constructed in the present invention. A. Detection of the expression of CD19 on the constructed Raji.Luc cell line and the isotype control Raji cell line respectively by using a CD19-specific antibody. B. Detection of the expression level of CD19 antigen in the constructed K562.CD19.Luc cell line and the control cell line respectively by using a CD19-specific antibody.

The monoclonal cells obtained above were identified for CD19 expression by flow cytometry. As shown in FIG. 2A, the expression of CD19 on the constructed Raji.Luc cell line and the isotype control Raji cell line (purchased from Miltenyi) was detected respectively by using a CD19-specific antibody. The flow cytometry results showed that the constructed Raji.Luc cell line had a higher CD19 expression level. FIG. 2B shows the expression level of CD antigen in the constructed K562.CD19.Luc cell line and the control cell line respectively detected by using a CD19-specific antibody. The flow cytometry results showed that the constructed K562.CD19.Luc cell line also had a very high CD19 expression level.

Example 3 Preparation of Immune Effector Cells Modified by the Chimeric Antigen Receptor and Detection of Killing Activity In Vitro (I) Preparation of T Lymphocytes 50 mL fresh blood from healthy human was collected, and peripheral blood mononuclear cells (PBMC) were separated by a lymphocyte separation solution and a density gradient centrifugation method. The cells were magnetically labelled using a Pan T Cell Isolation Kit (purchased from Miltenyi Biotech), and T lymphocytes were separated and purified. The purified T cells were then subjected to T lymphocyte activation and proliferation using CD3/CD28 magnetic beads.

(II) Transduction of T Lymphocytes with Lentivirus

The activated T lymphocytes were collected and resuspended in RPMI1640 culture medium. $1 \times 10^6$ activated T lymphocytes were infected with lentivirus, the cell suspension was added to a 6-well plate and incubated overnight at 37° C. in a 5% $CO_2$ incubator. On the next day, centrifugation was performed again and a fresh culture medium was replaced. A fresh culture medium was added every 3 days to continue the expansion culture.

(III) Detection of CAR-T Expression

The CAR-T cells prepared according to the above-mentioned protocol were collected by centrifugation, washed respectively three times with DPBS, and then genomic DNA was prepared using a human genome extraction kit (Gentra Puregene Cell Kit (purchased from Qiagen)). The prepared DNA was detected for the absorbance of $OD_{260\ nm}$ and $OD_{280\ nm}$ and then the concentration was calculated. The appropriate DNA concentration was adjusted. The Q-PCR reaction system was configured according to the kit SYBR Green Real time PCR Master mix plus (purchased from Toyobo). Then the gene copy number was detected on a fluorescence quantitative PCR machine (ABI #7300). The Q-PCR detection used accurately quantified plasmids containing the target fragments as positive control and for a standard curve. The CT value of each copy number concentration obtained by the Q-PCR and the corresponding copy number were plotted as a straight line and fit into a standard curve. The relative copy number for other test samples were calculated based on the fitted equation of the standard curve.

For the detection of the chimeric antigen receptor expressed in CAR-T cells in the present invention, the untransduced T lymphocyte (UnT) was used as a blank control, and the CD19 CAR-T (CAR2-T) comprising a CD8α signal peptide, a hinge region and a transmembrane region structures in the U.S. Pat. No. 8,399,645 B2 was used as a control.

The results of the detection of CAR integration copy number are shown in Table 1. The results showed that the integration of CAR1 gene was detected in the cell genome in the CAR1-T group, with the copy number of $7.46 \times 10^5$ copies/ng genomic DNA; the copy number of the transduced CAR2 gene was $12.90 \times 10^5$ copies/ng genomic DNA in the CAR2-T group; the measurements were extremely low (about 30 copies/ng genomic DNA) in the blank control UnT group and the $H_2O$, which belong to the background of the test.

TABLE 1

The copy number of CAR gene integrated into the donor T cell genome detected by the Q-PCR method

| Test samples | Ct value repeat 1 | Ct value repeat 2 | Average Ct value | Integrated copy number/ng genomic DNA |
|---|---|---|---|---|
| CAR1-T | 21.14 | 20.88 | 21.01 | 74643.34 |
| CAR2-T | 20.06 | 20.18 | 20.12 | 129031.70 |
| UnT | 34.10 | 33.41 | 33.76 | 30.31 |
| $H_2O$ | 33.70 | 33.06 | 33.38 | 38.16 |

Example 4 Detection of Killing Activity In Vitro

The CAR-T cells prepared above were collected, adjusted to a suitable density with R10 culture solution, and inoculated in a 384-well plate. CAR-T cells was co-cultured with the target Raji-Luc cells at an effector-to-target ratio (E:T) of 50:1 or 20:1 at 37° C. for 20 h. Then an equal amount of luciferase activity detection reagent One-Glo™ Luciferase Assay (purchased from Promega) was added. After the completion of the co-culture, the relative luciferase activity (RLU, relative light unit) remained in the reaction wells corresponds to the relative amount of viable cells in the wells. If the revealed luciferase RLU value is high, it means that there are many target cells which are not killed remained in the reaction wells, indicating that the cell killing activity in the wells is weak; conversely, if the revealed luciferase RLU value is low, it means that there are few target cells which are not killed in the reaction wells, indicating the cell killing activity in the well is strong. For the killing test of the CAR-T cells of the present invention against tumor cells, the untransduced T lymphocyte (UnT) was used as a blank control and CAR2 was used as a control.

Figure 3:
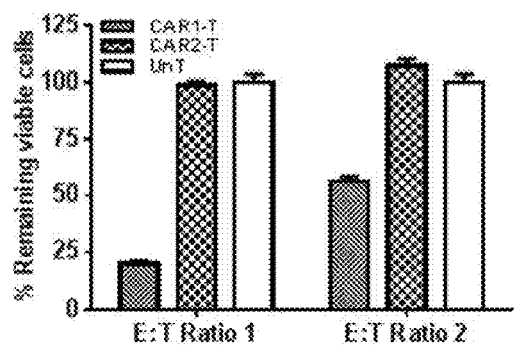
FIG. 3 is a graph showing the effect of CAR-T killing CD19-positive cells in vitro. A. Under the condition of E:T ratio 1, the relative proportion of the remaining Raji.Luc cells was 20.2%±1.23% after the co-culture of CAR1-T with Raji.Luc, while the relative proportion of the remaining Raji.Luc cells was 98.84%±1.60% in the CAR2-T group and 100%±3.54% in the UnT group; under the condition of E:T ratio 2, the relative proportion of the remaining Raji.Luc cells was 50.09%±2.17% after the co-culture of CAR1-T with Raji.Luc, while the relative proportion of the remaining Raji.Luc cells was 107.07%±3.04% in the CAR2-T group and 100%±3.50% in the UnT group. B. The relative proportion of the remaining Raji.Luc cells was 26.83%±1.97% after the co-culture of CAR1-T with Raji.Luc, while the relative proportion of the remaining target cells was 36.86%±3.46% in the CAR3-T group and 100%±1.78% in the UnT group.
Figure 3:
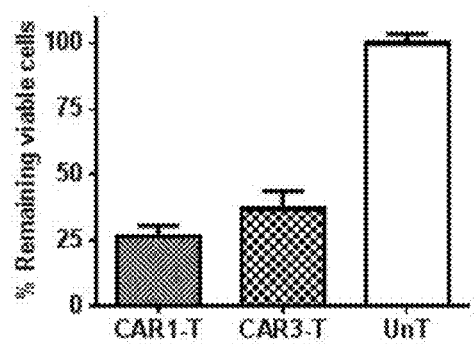
Figure 3:
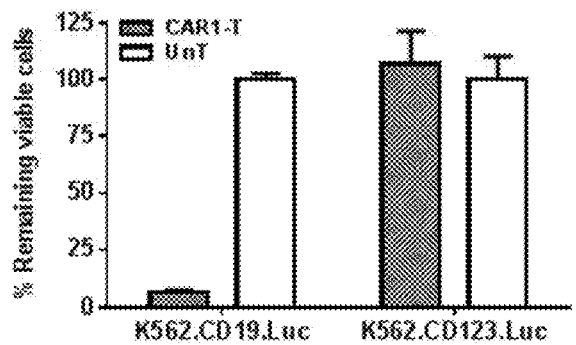

As shown in FIG. 3A, under the conditions of equivalent copy number of integration and different effector-to-target ratios (E:T ratio 1=50:1, E:T ratio 2=20:1), CAR1-T can significantly kill Raji. Luc cells (the relative luciferase activity RLU % was reduced), which was significantly better than the killing effect of CAR2-T in the control group. Under the condition of E:T ratio 1, the relative proportion of the remaining Raji.Luc cells was 20.2%±1.23% after the co-culture of CAR1-T with Raji.Luc, while the relative proportion of the remaining Raji.Luc cells was 98.84%±1.60% in the CAR2-T group and 100%±3.54% in the UnT group; under the condition of E:T ratio 2, the relative proportion of the remaining Raji.Luc cells was 50.09%±2.17% after the co-culture of CAR1-T with Raji.Luc, while the relative proportion of the remaining Raji.Luc cells was 107.07%±3.04% in the CAR2-T group and 100%±3.50% in the UnT group. The above results can reveal that CAR1-modified immune cells comprising the 4-1BB signal peptide and the transmembrane region domain and lacking the hinge region have a better in vitro tumor killing effect than the CAR2-modified immune cells comprising the CD8α signal peptide and the transmembrane region domain.

In another set of experiments, as shown in FIG. 3B, the relative proportion of the remaining Raji.Luc cells was 26.83%±1.97% after the co-culture of CAR1-T with Raji.Luc, while the relative proportion of the remaining Raji.Luc cells was 36.86%±3.46% in the CAR3-T group and 100%±1.78% in the UnT group. CAR1 differs from CAR3 in that the extracellular signal peptide is different, and CAR3 comprises the CD8α signal peptide. From the results of FIG. 3B, it can be inferred that CAR1-modified immune cells comprising the 4-1BB signal peptide and the transmembrane region have a better in vitro tumor killing effect than the CAR3-modified immune cells comprising the CD8α signal peptide.

Combining the data from FIGS. 3A and 3B, it can be inferred that the immune cells modified by the chimeric antigen receptors comprising different signal peptides or transmembrane region structures have different in vitro killing ability, and the transmembrane region structure may have more significant impacts on the performance of the chimeric antigen receptor.

Further, in the target-specific killing experiments, the present invention used the constructed K562.CD19.Luc expressing CD19 and the K562.CD123.Luc stable cell line not expressing CD19 but expressing CD123 (Example 2) to evaluate the specificity of the killing effect of CAR1. As shown in FIG. 3C, the relative proportion of the remaining K562.CD19.Luc cells was 6.77%±0.84% after the co-culture of CAR1-T with K562.CD19.Luc; while the relative proportion of the remaining K562.CD123.Luc cells was 107.06%±14.39% after the co-culture of CAR1-T with K562.CD123.Luc; however, the UnT cells had no obvious killing effect on both target cells; and CAR1-T had an obvious target-selective killing effect on K562.CD19.Luc cells.

Example 5 Detection of IFNγ Release Level in CAR-T Cells

The CAR-T cells prepared above were collected, and adjusted to an appropriate density with R10 culture solution and inoculated in a 96-well plate. The release of IFNγ is a hallmark of T cell activation. In this example, different CAR-T cells were co-cultured with target cells at E:T=20:1 at 37° C. Then the co-cultured supernatant was removed. Using a real-time fluorescence resolution technology kit (Homogeneous Time Resolved Fluorescence (HTRF), Cisbio #64IL2PEB), the amount of IFN-γ released in the supernatant was detected. At the same time, CAR2-T was used as a control, the untransduced T lymphocyte (UnT) and the T lymphocyte (Luc) transduced only with viral vector were used as blank controls.

Figure 4:
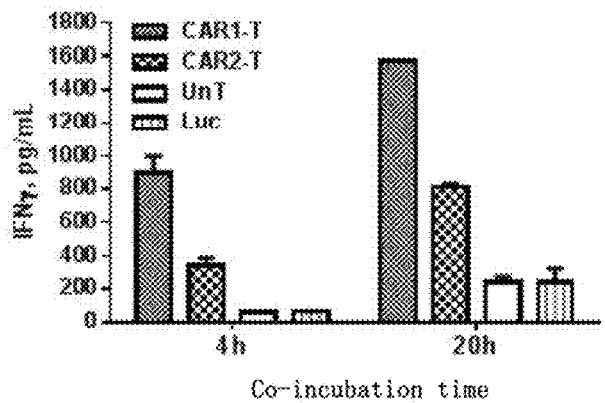
FIG. 4 shows the detection OF IFNγ release level in CAR-T cells. A. The amount of IFNγ released after co-incubation with Raji.Luc cells for 4 h and 20 h in the CAR1-T, CAR2-T and UnT, Luc groups. B. The amount of IFNγ released after co-incubation with the B lymphocytes from patients with B cell acute lymphoblastic leukemia for 4 h and 20 h in the CAR1-T, CAR2-T and UnT, Luc groups.
Figure 4:
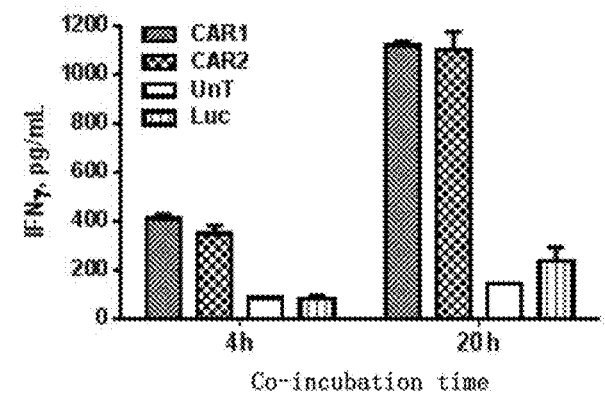

As shown in FIG. 4A, after CAR-T cells or UnT cells were co-incubated with CD19-positive Raji.Luc cells for 4 h, the amount of IFNγ released in the CAR1-T group was 894.49±101.64 pg/mL, the amount of IFNγ released in the CAR2-T group was 343.88±44.30 pg/mL, the amount of IFNγ released in the UnT group was 59.49±6.52 pg/mL, and the amount of IFNγ released in the Luc group was 67.43±1.52 pg/mL; after co-incubation for 20 h, the amount of IFNγ released in the CAR1-T group was 1572.23±0.60 pg/mL, the amount of IFNγ released in the CAR2-T group was 808.67±21.42 pg/mL, the amount of IFNγ released in the UnT group was 240.82±34.11 pg/mL, and the amount of IFNγ released in the Luc group was 239.82±83.47 pg/mL. Compared with the UnT and Luc controls, CAR1-T and CAR2-T can significantly release IFNγ, and CAR1-T has a more prominent antigen-dependent IFNγ release level than CAR2-T.

As shown in FIG. 4B, after CAR-T cells or UnT cells were co-incubated with the B lymphocytes from patients with B cell acute lymphoblastic leukemia (B-ALL) for 4 h, the amount of IFNγ release in the CAR1-T group was 411.73±16.14 pg/mL, the amount of IFNγ released in the CAR2-T group was 349.41±43.09 pg/mL, the amount of IFNγ released in the UnT group was 88.66±2.42 pg/mL, and the amount of IFNγ released in the Luc group was 82.87±14.24 pg/mL; after co-incubation for 20 h, the amount of IFNγ released in the CAR1-T group was 1119.37±18.045 pg/mL, the amount of IFNγ released in the CAR2-T group was 1099.93±75.93 pg/mL, the amount of IFNγ released in the UnT group was 146.04 pg/mL, and the amount of IFNγ released in the Luc group was 236.45±57.50 pg/mL. Compared with the UnT and Luc control groups, both CAR1-T and CAR2-T can have a significant IFNγ release amount, and CAR1-T have a slightly higher IFNγ release level than the CAR2-T control group.

Example 6 Clinical Trial Treatment Effect of the CAR1 Transduced Autologous T Cells on the Patients with CD19-Positive B Cell Acute Lymphoblastic Leukemia The peripheral blood of patients with acute B cell lymphoblastic leukemia was collected. The T cells were separated and purified (Example 2), and were transduced with CAR1 lentivirus vectors after 2 days of in vitro activation. After transduction, centrifugation was performed, and the CAR1 lentivirus vector that did not enter the cells in the culture supernatant was washed away. The transduced T cells were resuspended in the culture medium containing IL-2 at a final concentration of 100 IU/mL and CD3/CD28 magnetic beads. On the next day, the expansion culture was performed at a culture density of $0.5$-$2\times10^6$/ml for 11-14 days.

Figure 5:
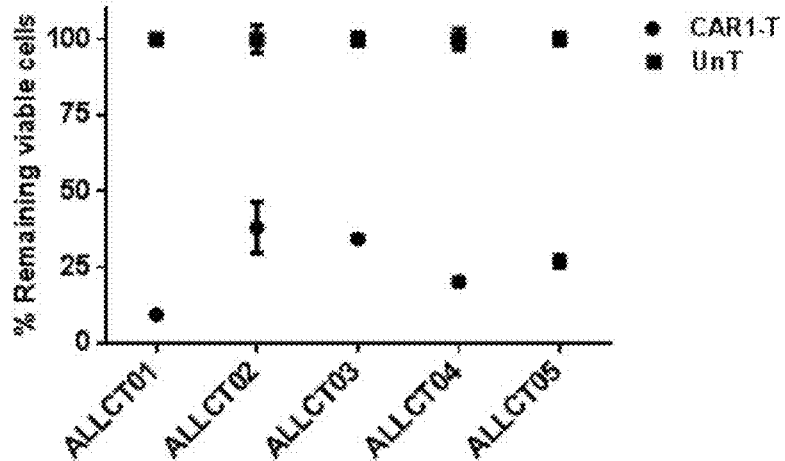
FIG. 5 shows the detection of tumor killing effect of the autologous T cells transduced with CAR1. CAR1 was transduced into T cells from 5 different B-ALL patients, respectively, and the transduced cells were named ALLCT01, ALLCT02, ALLCT03, ALLCT04 and ALLCT05, respectively. After the co-incubation of the CAR1 transduced cells with Raji.Luc target cells, the relative number of the remaining Raji.Luc cells was 9.33%-37.82%.

CAR1 was transduced into T cells from 5 different B-ALL patients, respectively, and the transduced cells were named ALLCT01, ALLCT02, ALLCT03, ALLCT04 and ALLCT05, respectively. The results in FIG. 5 showed that all the cells transduced with CAR1 demonstrated strong ability of killing Raji.Luc target cells in vitro, and the relative number of the remaining Raji.Luc cells was 9.33%-37.82% after co-incubation with the Raji.Luc target cells.

The following contents exemplify the CD19 CAR-T treatment in ALLCT01 patient with acute B lymphoblastic leukemia.

ALLCT01 patient: through the examination in the hospital, the disease was manifested as active bone marrow hyperplasia, abnormal lymphocyte system hyperplasia, 65% of original lymphocytes, dominant mast cells, irregular edges, relative more cytoplasm, irregular karyotype, visible depression and folding, reduced granulocyte system proliferation, reduced red blood cell system proliferation, and rare platelets, which was clinically diagnosed as B-ALL (NR). After the hospital has made the recommendation and the ethical review has passed, the patient signed the informed consent form, and then the clinical trial study of CAR-T cell treatment was performed.

The process of the CAR-T cell treatment was: collecting the peripheral blood of the patient, separating and purifying T cells in vitro, preparing CD19 CAR-T cells in vitro, autologously re-infusing into the patient intravenously at three time points. About $1.5\times10^8$ cells was infused totally.

Figure 6:
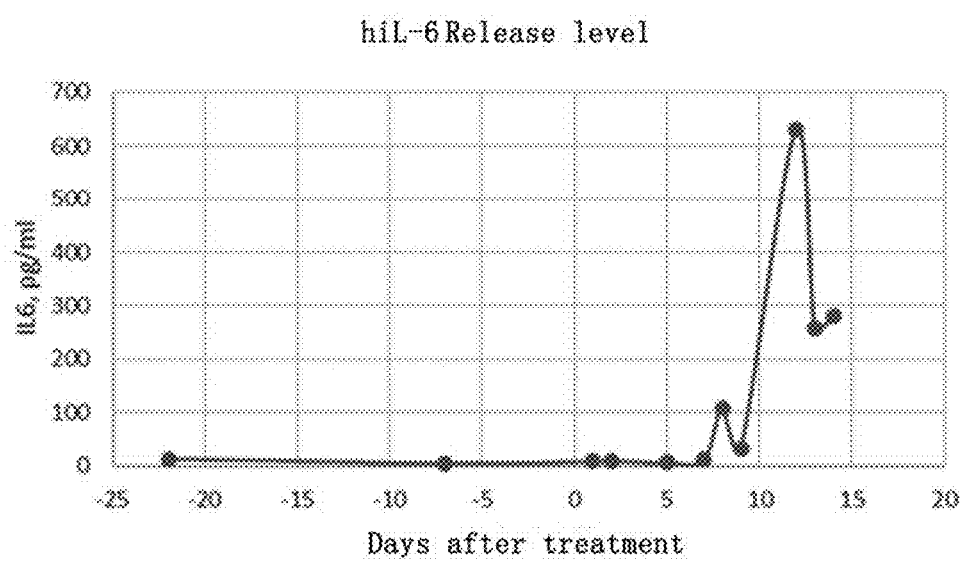
FIG. 6 is a graph showing the release level of human interleukin 6. After the ALLCT01 patients were re-infused with CD19 CAR-T cells, the body temperature began to rise at day 6 after the last re-infusion, and the cytokine test results showed that the secretion level of interleukin-6 (IL-6) was significantly increased.

After the ALLCT01 patients were re-infused with CD19 CAR-T cells, a relatively mild response occurred: the body temperature began to rise at day 6 after the last re-infusion; the cytokine test results showed that the secretion level of interleukin-6 (IL-6) was significantly increased (FIG. 6); and fever lasted for 6 days and the body temperature did not exceed 40° C. The symptomatic treatment was performed by infusing a small amount of IL-6R monoclonal antibody Tocilizumab 3 days after the fever, and then the body temperature gradually decreased and reached the normal body temperature after 4 days. However, generally the B-ALL patients who had received the CD19 CAR-T treatment had high fever within 3 days in the foreign reports. The results of this test indicate that the CD19 CAR (CAR1) of the present invention has a milder response in the treatment of B-ALL and has less side effects in patients.

The peripheral blood of the patients was tested 14 days after the last re-infusion. As shown in the results of Table 2, the percentage of CD19-positive (CD19+) cells in peripheral blood decreased from 63% before treatment to 0%, and 83.59% of the cells were CD3-positive (CD3+) cells. Combined with the results of hematological detection, it was shown that the CD19-positive leukemia cells in the peripheral blood were completely eliminated after the patient was treated with the CD19 CAR-T cells provided in the present invention, and the clinical complete remission was achieved.

TABLE 2

Changes of T and B lymphocytes in the hemogram before and after the CAR-T treatment in B-ALL patients

| Detection item | Before | Detection at day 14 |
| --- | --- | --- |
| CD19+ cells | 62.80% | 0% |
| CD3+ cells | 22% | 83.59% |
| CD3+ CD4+ cells | 14.30% | 54.01% |
| CD3+ CD8+ cells | 14.20% | 22.72% |

The experimental methods not recorded in detail in the present application document are all conventional techniques in the art, and can be realized by the literature or technical means before the filing date.

The invention claimed is:

1. A chimeric antigen receptor, comprising an extracellular signal peptide, an antigen binding domain, a transmembrane domain and an intracellular signal domain, wherein said extracellular signal peptide is selected from one of a 4-1BB signal peptide, a CD8α signal peptide, a GM-CSFRα signal peptide or a CD4 signal peptide, and the transmembrane domain is a 4-1BB molecular transmembrane region sequence, wherein the antigen bound by the antigen binding domain is CD19, and wherein the antigen binding domain comprises an amino acid sequence as set forth in SEQ ID NO. 9.

2. The chimeric antigen receptor according to claim 1, wherein an amino acid sequence of a 4-1BB molecular transmembrane region as said transmembrane domain is as set forth in SEQ ID NO. 1, or a polypeptide having 85%-99% identity with the amino acid sequence of SEQ ID NO. 1.

3. The chimeric antigen receptor according to claim 1, wherein said extracellular signal peptide is selected from a 4-1BB signal peptide with an amino acid sequence as set forth in SEQ ID NO. 2, or a polypeptide having 85%-99% identity with the amino acid sequence of SEQ ID NO. 2.

4. The chimeric antigen receptor according to claim 1, wherein an antibody from which the antigen binding domain is derived is selected from a monoclonal antibody, Fab, or scFv.

5. The chimeric antigen receptor according to claim 1, wherein the intracellular signal domain comprises an intracellular signaling domain and/or a co-stimulatory signal domain and is selected from intracellular domains of the following signal molecules: CD3ζ, CD3 gamma, CD3 delta, CD3 epsilon, common FcR gamma, FcR beta, CD79a, CD79b, Fc gamma RIIa, DAP10, DAP12, CD27, CD28, 4-1BB, OX40, CD30, CD40, CD2, lymphocyte function-associated antigen-1, LIGHT, NKG2C, B7-H3, PD-1, ICOS, CDS, ICAM-1, GITR, BAFFR, HVEM, SLAMF7, CD7, NKp80, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1, SLAMF4, CD84, CD96, CEACAM1, CRTAM, Ly9, CD160, PSGL1, CD100, CD69, SLAMF6, SLAM, BLAME, SELPLG, LTBR, LAT, GADS, SLP-76, PAG/Cbp, NKp44, NKp30, NKp46, NKG2D, a ligand specifically binding to CD83, or any combination thereof.

6. The chimeric antigen receptor according to claim 5, wherein the intracellular signal domain comprises a CD3ζ, 4-1BB and/or CD28 signal domain.

7. The chimeric antigen receptor according to claim 6, wherein the intracellular signal domain comprises a 4-1BB intracellular co-stimulatory signal domain with an amino acid sequence as set forth in SEQ ID NO. 6.

8. The chimeric antigen receptor according to claim 6, wherein the intracellular signal domain comprises a CD28 intracellular co-stimulatory signal domain with an amino acid sequence as set forth in SEQ ID NO. 7.

9. The chimeric antigen receptor according to claim 6, wherein the intracellular signal domain comprises a CD3ζ intracellular signalling domain with an amino acid sequence as set forth in SEQ ID NO. 8.

10. The chimeric antigen receptor according to claim 1, wherein said chimeric antigen receptor comprises a 4-1BB signal peptide or CD8α signal peptide, an antigen binding domain, a 4-1BB transmembrane domain, a 4-1BB and/or CD28 intracellular co-stimulatory binding domain, and a CD3 intracellular signalling domain which are sequentially connected.

11. The chimeric antigen receptor according to claim 10, wherein said chimeric antigen receptor further comprises a hinge region between an extracellular antigen binding domain and the transmembrane domain.

12. The chimeric antigen receptor according to claim 10, wherein said chimeric antigen receptor comprises an amino acid sequence as set forth in SEQ ID NO. 10 or SEQ ID NO. 12, or an amino acid sequence having 85%-99% identity with SEQ ID NO. 10 or SEQ ID NO. 12.

13. A nucleic acid encoding the chimeric antigen receptor of claim 1.

14. The nucleic acid according to claim 13, wherein the nucleic acid is selected from a nucleotide sequence as set forth in SEQ ID NO. 22 or SEQ ID NO. 24.

15. A recombinant expression vector, comprising the nucleic acid molecule of claim 13.

16. A cell expressing the chimeric antigen receptor of claim 1.

17. The cell according to claim 16, wherein said cell is an immune cell.

18. The cell according to claim 17, wherein said cell is selected from T lymphocyte, NK cell, or an immune cell differentiated by culturing a hematopoietic stem cell, a pluripotent stem cell or an embryonic stem cell.

19. A method for preparing a T cell modified by the chimeric antigen receptor, wherein the method comprises separating and activating the T cell to be modified, and then transducing the T cell with the recombinant expression vector of claim 15.

20. A pharmaceutical composition, comprising an effective amount of the cell of claim 16 and a pharmaceutically acceptable carrier.

21. A method of treating a tumor that expresses CD19 in a patient, the method comprising administering to the patient an effective amount of the cell of claim 16.

22. A method of treating a tumor that expresses CD19 in a patient, the method comprising administering to the patient an effective amount of the pharmaceutical composition of claim 20.

* * * * *